United States Patent
Kenel et al.

(10) Patent No.: US 6,548,022 B1
(45) Date of Patent: Apr. 15, 2003

(54) AUTOMATIC ANALYZER

(75) Inventors: Urs Kenel, Baar (CH); Jurgen Rauh, Grenzach-Wyhlen (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/302,743

(22) Filed: Apr. 30, 1999

(30) Foreign Application Priority Data

May 1, 1998 (EP) .................................. 98810393

(51) Int. Cl.$^7$ ..................... G01N 15/06; G01N 33/00; G01N 21/00; G01N 1/10; B01L 3/00; B01F 15/02; B01F 5/06

(52) U.S. Cl. ................. 422/68.1; 422/73; 422/63; 422/102; 436/180; 366/130; 366/191; 366/336

(58) Field of Search ................ 422/102, 63, 68.1, 422/65, 73; 366/336, 191, 130, 143; 436/180

(56) References Cited

U.S. PATENT DOCUMENTS

| | | | |
|---|---|---|---|
| 3,674,672 A | | 7/1972 | Whitesell |
| 4,734,262 A | * | 3/1988 | Bagshawe |
| 4,902,481 A | * | 2/1990 | Clarke et al. |
| 5,174,966 A | * | 12/1992 | Durnad et al. |
| 5,409,833 A | * | 4/1995 | Hu et al. |
| 5,419,874 A | * | 5/1995 | Coassin et al. |
| 5,484,572 A | * | 1/1996 | Katakura et al. |
| 5,595,653 A | * | 1/1997 | Good et al. ............ 210/289 |
| 5,602,037 A | * | 2/1997 | Ostgaard ................ 436/69 |
| 5,603,900 A | * | 2/1997 | Clarke et al. |
| 5,746,975 A | * | 5/1998 | Château |
| 5,855,848 A | * | 1/1999 | Zuccato |
| 5,993,742 A | * | 11/1999 | Binz et al. .............. 422/81 |
| 6,092,921 A | * | 7/2000 | Wentinck et al. ........ 366/174.1 |
| 6,309,605 B1 | * | 10/2001 | Zermani |

FOREIGN PATENT DOCUMENTS

| | | |
|---|---|---|
| EP | 0 787 990 A | 8/1997 |
| WO | WO 97 39359 A | 10/1997 |

OTHER PUBLICATIONS

COBAS Integra, Revision History, ISE Update Version 1.0, pp. 0.2, 1.4, 2.8 and 2.9, Revision Date: Oct. 1997.

Patents Abstracts of Japan Vo.. 014 No. 558 (P–1141) & JP 02 238363 A, Dec. 12, 1990 & Oct. 20, 1990; Meidensha Corp.

* cited by examiner

*Primary Examiner*—Jill Warden
*Assistant Examiner*—Brian R Gordon
(74) *Attorney, Agent, or Firm*—Gibbons, Del Deo, Dolan, Griffinger & Vecchione

(57) ABSTRACT

The automatic analyzer for the assay of liquid samples comprises an exchangeable mixing chamber whose mixing chamber is tapered toward the bottom and is provided with an outlet which is followed by a bore which connects the mixing chamber to an outlet opening. An abrupt transition is formed between said bore and the outlet opening for the analyzed liquid. The abrupt transition is a restriction which serves as a collecting trap for disturbing particles, e.g. coaguli, which might lead to undesirable obstructions elsewhere. Those particles which cannot be flushed away laterally by another outlet opening are eliminated by removing the mixing chamber from the base and blowing it through. A sealing ring serves for a tight seal between the plane bottom of the mixing chamber and the connection. A fluid sensor is provided in order to detect the sample liquid flowing through this connection.

12 Claims, 4 Drawing Sheets

AUTOMATIC ANALYZER

RELATED APPLICATION

This application is related to the European Patent Application No. 98810393.3 filed on May 1, 1998.

BACKGROUND OF THE INVENTION

1. Field of the Invention

The present invention refers to an automatic analyzer for the assay of liquid samples, said automatic analyzer comprising a mixing chamber which is followed by an analyzing block including an evaluating unit, said mixing chamber comprising at least one inlet opening for air and water respectively and being connected to an outlet opening for the analyzed liquid.

2. Description of the Prior Art

As an example of the prior art, FIG. 1 shows an automatic analyzer for the selective determination of ions, e.g. $Li^+$, $K^+$, $Cl^-$, in liquid samples of biological substances such as blood or urine. The samples are placed on a sample platform in separate containers. By means of an automatic pipette arm 12 small amounts of the samples are serially supplied to a mixing chamber. The chamber essentially consists of an upwardly open, cylindrical vessel having a continuously tapering bottom. Inlet openings for air and water, respectively, are laterally connected to the top of this vessel, and two outlet openings are connected to its bottom. The liquid samples delivered by the pipette needle are homogenized by means of an air vortex generated by an opening, and supplied by an outlet opening and a connecting duct to the measuring channel of an analyzing block, such as an electrode block. A second inlet opening mainly serves for the supply of rinsing water and an outlet opening for the extraction of the latter and of possible excess liquid (waste).

The measuring channel of the analyzing block is provided with several ion-selective electrodes and a reference electrode connected thereto which measure the ion concentration of the above-mentioned ions and output the measuring results by means of an electronic evaluating system. Finally, the sample liquid is discharged into a collector 25 for disposal.

The operation of automatic analyzers of the represented kind should be as free of disturbances as possible. However, since the analyzed liquids come from a large number of sources, this aim can only be attained within certain limits. In particular, frequent problems are caused by small particles such as coaguli which may choke the analyzer, thereby resulting in incorrect analyses or even rendering the measurements impossible. In such cases, the critical components must be disassembled and cleaned, thereby causing complications and time losses.

SUMMARY OF THE INVENTION

It is an object of the present invention to provide an improvement of known automatic analyzers by preventing the described obstructions as much as possible.

The present invention provides for an automatic analyzer wherein the mixing chamber is disposed in a dedicated, exchangeable unit, and the outlet opening for the analyzed liquid is associated with a particle collecting trap.

In particular, an advantage of the present invention is that the mixing chamber is easily exchangeable, so that impairments of the operation of the automatic analyzer by an obstruction of the mixing chamber by a particle, e.g. a coagulum, are easily and quickly eliminated. Furthermore, the mixing chamber design of the present invention allows quick and effective cleaning, so that possible particles in its outlet channel are easily removed.

DETAILED DESCRIPTION OF THE INVENTION

Figure 1:
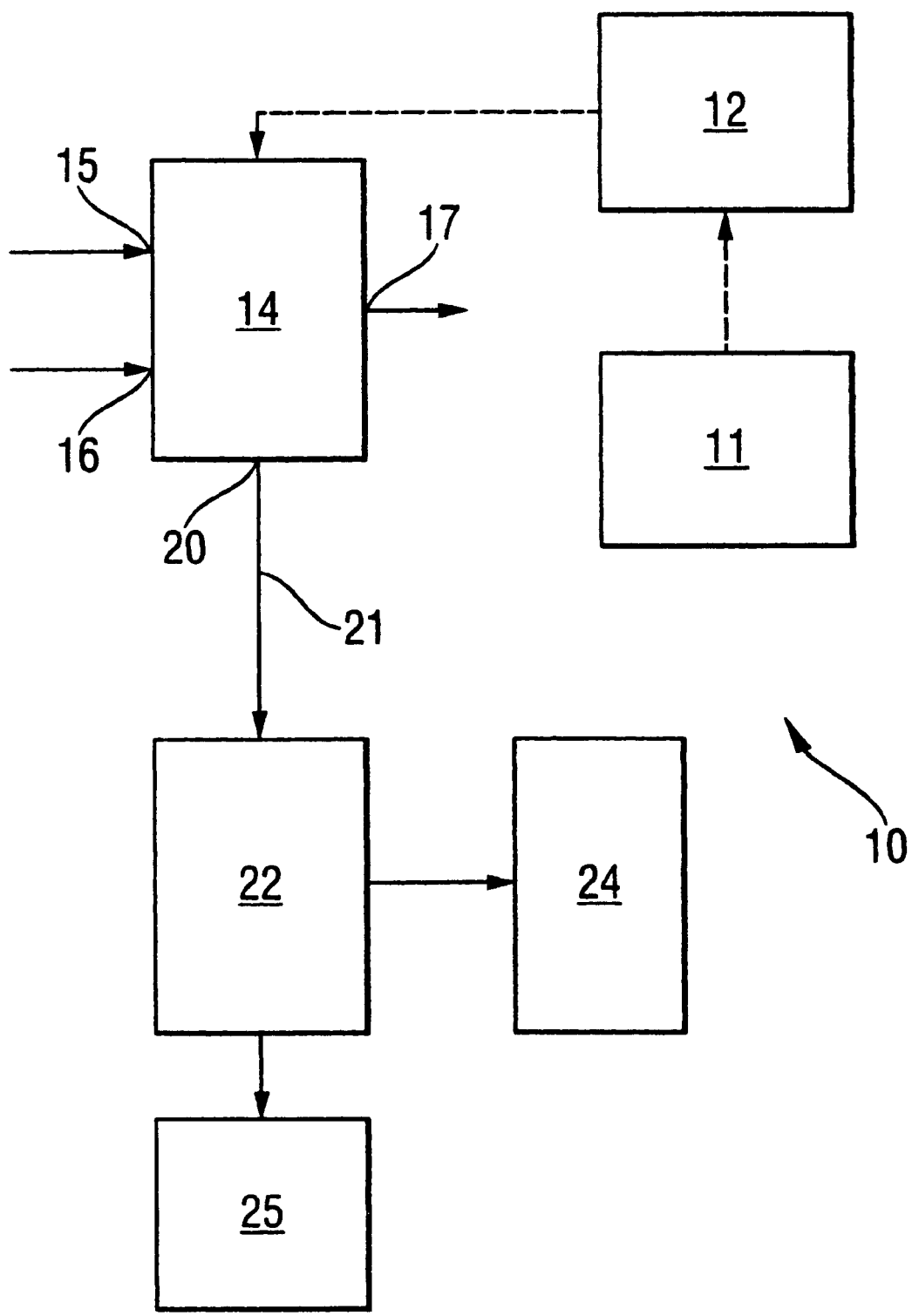
FIG. 1 is a block diagram of an automatic analyzer of the prior art as previously discussed above.

The present invention refers to an automatic analyzer 10 for the assay of liquid samples. As shown by FIG. 1 analyzer 10 has at least a vertically extending mixing chamber 14 with at least one inlet opening 15 and 16 for air and water, respectively. There is an outlet opening 20 for the analyzed liquid as well as an analyzing block 22 following the mixing chamber 14 and including an evaluating unit 24 wherein the mixing chamber 14 is disposed in a dedicated, exchangeable unit. According to the invention the outlet opening 20 for the analyzed liquid is associated with a collecting trap for particles 23.

Figure 2:
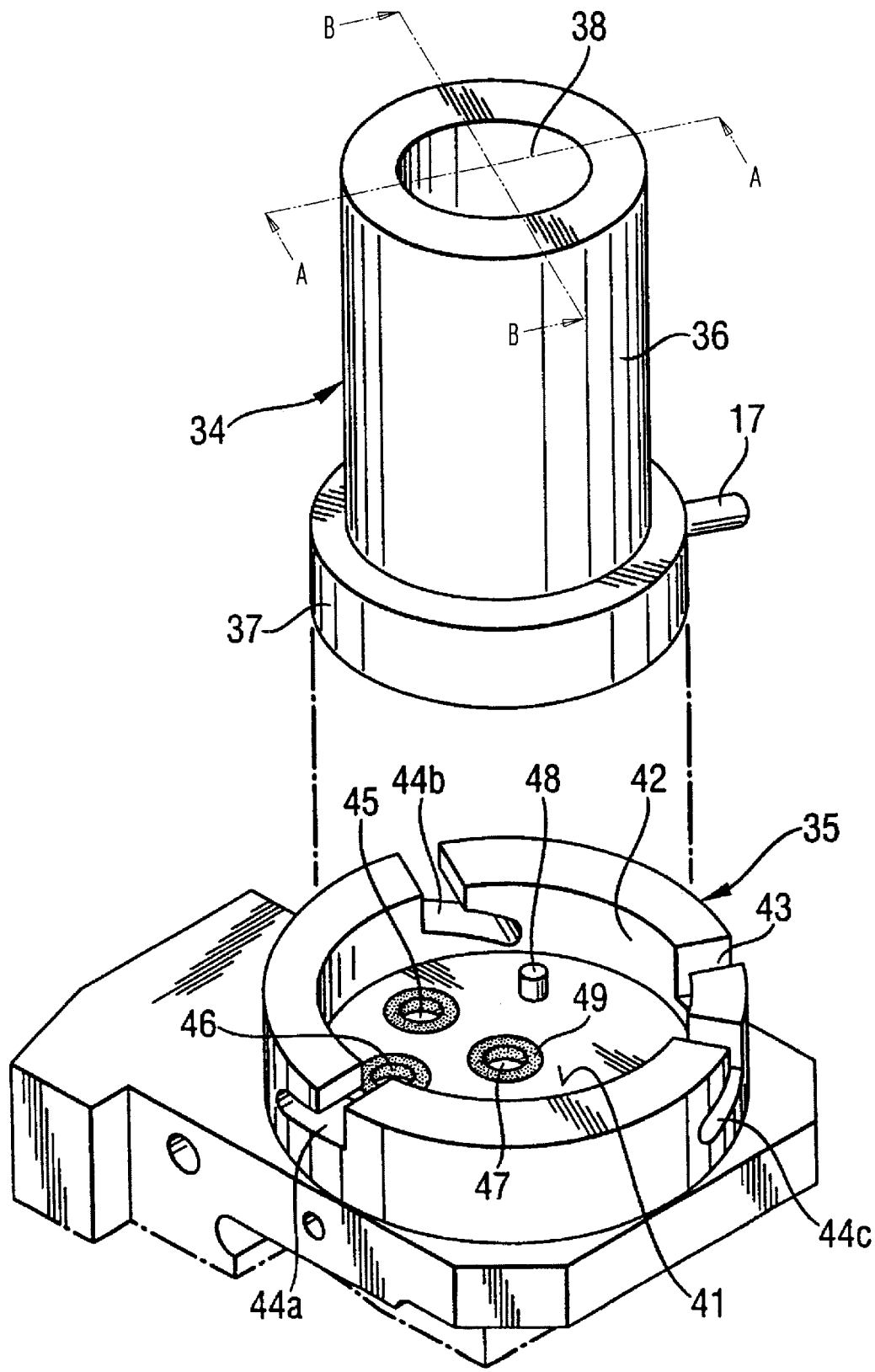
FIG. 2 is a perspective view of a mixing chamber and the associated base.

FIG. 2 illustrates a mixing chamber 34 and an associated base 35 in a perspective view. The mixing chamber 34 is provided with an essentially cylindrical outer wall 36 which is seamlessly followed at the bottom by a base plate 37 of a larger diameter. The first outlet opening 17 laterally projects from plate 37 in the form of a connecting nipple which allows the connection of a drain water tube. The mixing chamber 34 is open at the top (sample opening 38) and comprises a plane bottom. The latter communicates with outlet opening 17, which is hidden in the illustration. Furthermore, in FIG. 3 one riser 30 leads up from the bottom into wall 36 of mixing chamber 34 and communicates with the inlet opening 15. The mixing chamber 34 consists of a transparent material.

The base 35 constitutes the counterpart of mixing chamber 34 in automatic analyzer 10. Accordingly, the base 35 has a plane bottom 41 which is cylindrically surrounded by a cylindrical guide 42 adapted to an insertable base plate 37. The cylindrical guide 42 is provided with an incision 43 for the reception of an outlet opening 17 and with three locking slots 44a, 44b and 44c. The bottom 41 communicates with connection 45 of the air riser, with connection 46 of the water riser, and with connection 47 of the second outlet opening 20 for the analyzed liquid. The present invention further provides a pin 48 which cooperates with a non-represented blind bore of the base plate 37 to allow a correct angular guidance of the mixing chamber 34 while it is inserted into the base 35.

Connections 45, 46 and 47 are provided with sealing rings 49 (FIG. 3), preferably exchangeable, which ensure a tight connection with openings 15, 16, and 20, respectively. The mixing chamber 34 is attached to the base 35 by a non-represented coupling ring which is slipped over the mixing chamber 34 from above and seizes the upper edge of the base plate 37, and which is secured by a clockwise rotation by means of internal pins which engage in locking slots 44a, 44b, and 44c.

Figure 3:
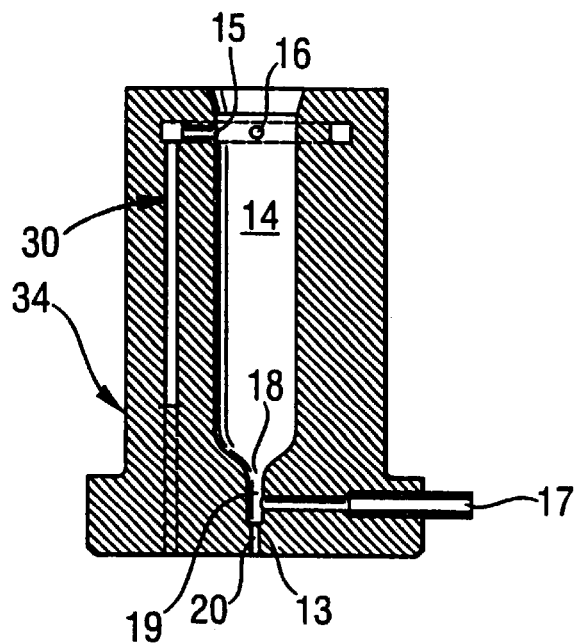
FIG. 3 is a cross-section of the mixing chamber taken along line A—A of FIG. 2.

FIG. 3 shows a central cross-section of the mixing chamber 34 at a scale of approx. 2:1 with respect to its real size. Upwardly open mixing chamber 14 is cylindrical in shape while its wall surface is as smooth as possible and is conically tapered at the bottom. At the pointed end of mixing chamber 14, the wall of the mixing chamber comprises an outlet opening 18 which is followed by a vertical bore 19 whose diameter width approximately corresponds to that of connecting duct 21 and of the measuring channel of analyzing block 22. This vertical bore 19 is horizontally connected to a first outlet opening 17. At the bottom, bore 19 is followed by a second outlet opening 20 whose diameter abruptly decreases at transition 13, the diameter being reduced to a third of the diameter of the bore 19. In a preferred embodiment, the values for the outlet opening 20 are from 0.3 to 0.4 mm and for the bore 19 is 0.8 mm. The restriction 13 serves as a trap for particles which are capable of causing the obstructions described.

Figure 5:
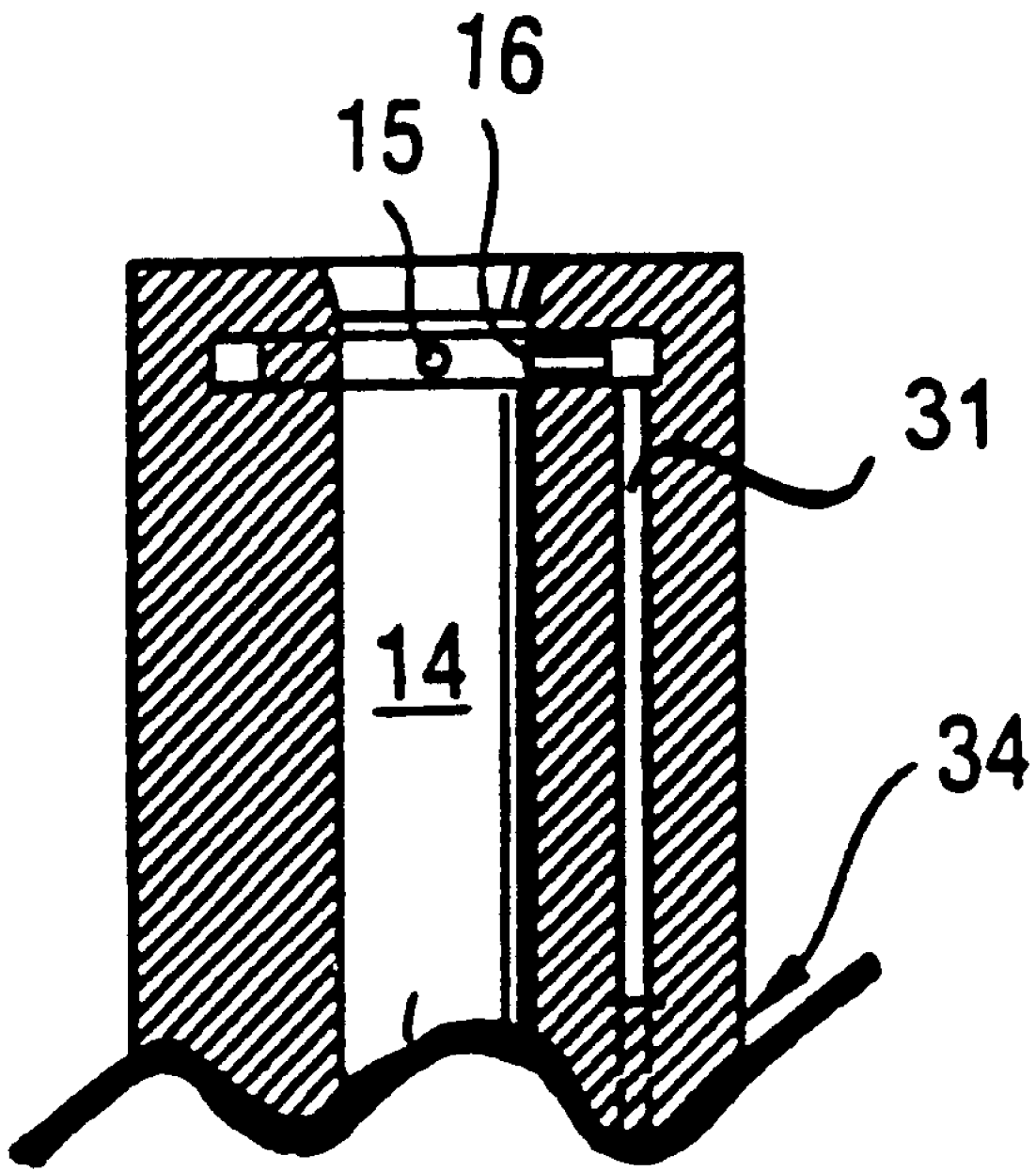
FIG. 5 is a partial cross-section of the mixing chamber taken along line B—B of FIG. 2.

FIG. 5 illustrates a central cross-section of the mixing chamber 34 at a scale of approximately 2:1, similar to FIG. 3. The upwardly open mixing chamber 14 is cylindrical in shape while its wall surface is as smooth as possible. The riser 31 leads up from the bottom of the wall of the mixing chamber and communicates with outlet 16.

Figure 4:
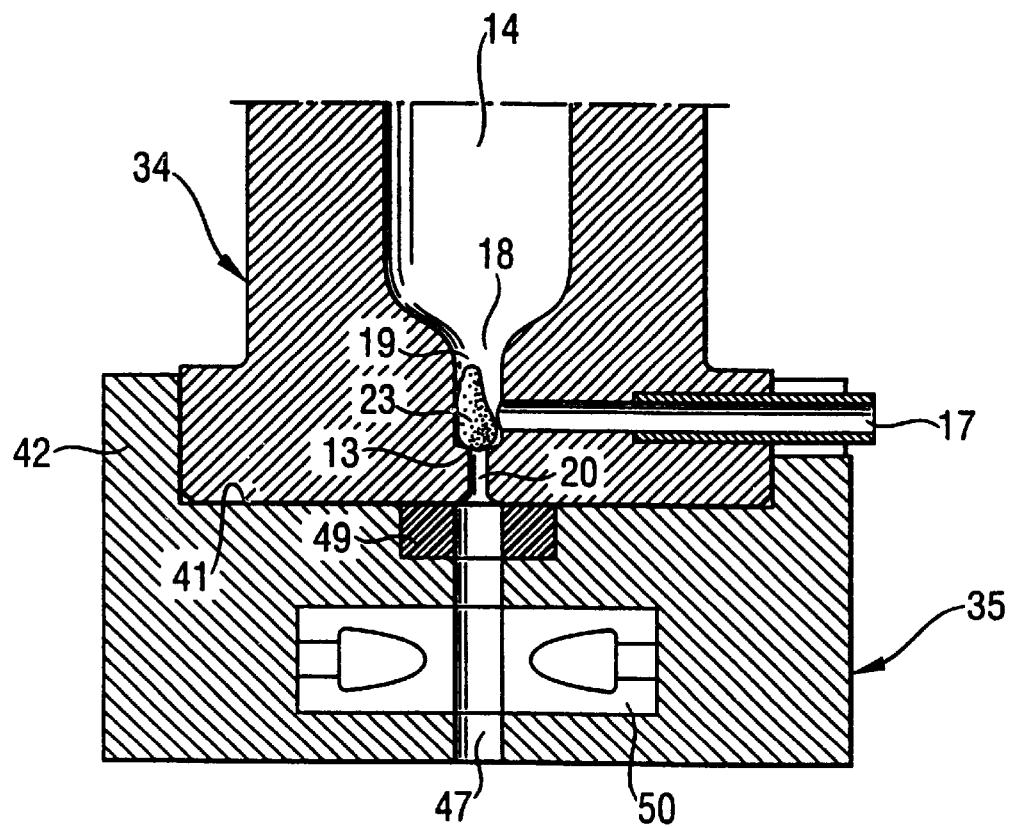
FIG. 4 is a cross-section of the mixing chamber and the base.

FIG. 4 shows another cross-section of the mixing chamber 34 and of the base 35 on a further enlarged scale. At the location of restriction 13 between bore 19 and second outlet opening 20, i.e. in the collecting trap, a particle 23 is shown whose travel in the direction of connection 47 is hindered. Particle 23 reduces or blocks the desired flow of the analyzed measuring liquid toward analyzing block 22. The occurrence of this condition is detected by a fluid sensor 50 at connection 47 which detects the absence of the expected liquid. In this case, the automatic analyzer can be stopped.

In order to eliminate such an obstruction, the blocking particle can be flushed by the supply of water from the inlet opening 16 and extracted by the lateral outlet opening 17. Alternatively, the mixing chamber 34 can be replaced by a spare unit, thereby restoring the operativeness of automatic analyzer 10. The mixing chamber 34 is also easily cleaned by flushing it from outlet opening 20 to the mixing chamber 14, so that the mixing chamber 34 is available as a new spare unit.

The described division of the automatic analyzer 10 into a base 35 and an easily exchangeable mixing chamber 34 having a particle trap is simple in construction and avoids prolonged failures of the analyzer 10. The fluid sensor 50 allows safe detection of a possibly required exchange and cleaning of the mixing chamber. Those solid constituents of the analyzed liquid which pass second outlet opening 20 do not impair the measurements in analyzing block 22 and do not constitute a risk of obstructions of the hitherto usual kind. The amount of time that the automatic analyzer 10 is not in operation as well as the time required for maintenance are thus substantially reduced.

In accordance with one aspect of the present invention, the shape of the mixing chamber does not necessarily have to be cylindrical. For example, it may be convex or have an oval cross-section. However, the container walls should be smooth to avoid material deposits. Furthermore, a tapered zone should be provided at the bottom in order to ensure draining of the liquid.

In accordance with another aspect of the present invention, the first outlet opening 17 for the drained liquid may be directed downwards instead of sideways.

In accordance with yet another aspect of the present invention, the attachment of the mixing chamber 34 in the base 35 may be obtained by different means such as by a lever closure.

In accordance with further aspect of the present invention, instead of the bore 19 and the outlet opening 20 whose cross-sections are both cylindrical, the particle trap may also be formed by non-cylindrical cross-sections such as by a trefoil cross-section of the outlet opening 20.

In accordance with another aspect of the present invention, the particle trap may be an integral part of the mixing chamber 34, as described above. It is also possible, however, to obtain the reduction of the width of the bore 19 by a separate part which is exchangeably disposed transversally or longitudinally in the bore such as by a nozzle screwed into bore 19.

It should be understood, however, that the present invention herein illustrated and described is intended to be representative only, as many changes may be made therein without departing with the clear teachings of the invention. Accordingly, reference should be made to the following claims in determining the full scope of the invention, as it will be appreciated that the invention is susceptible to modification, variation and change without departing from the proper scope and fair meaning of the subjoined claims.

What is claimed is:

1. An automatic analyzer for the assaying samples, said automatic analyzer comprising:

a chamber for mixing a liquid sample, said chamber having an outlet opening, and an evaluation unit for receiving said liquid sample from said chamber through said outlet opening, said evaluation unit determining at least one characteristic of said sample, and wherein said chamber has a trap for collecting particles which are suspended in the liquid sample prior to evaluation by said evaluation unit, said trap being formed by a portion of the walls of said chamber and said opening, said portion of said walls and said opening being operative to separate said suspended particles from said liquid sample.

2. The automatic analyzer of claim 1, wherein the mixing chamber has an associated volume and said trap collects the particles which are suspended in the liquid sample in a localized region of said chamber, said localized region being substantially smaller than said volume.

3. The automatic analyzer of claim 1, wherein said mixing taper to form a bore and then abruptly transition to form said outlet opening, said bore having a larger cross-section than that of said outlet opening, said bore having a larger cross-section than that of said outlet opening and said trap being formed by the substantially abrupt transition between said bore and said outlet opening.

4. The automatic analyzer of claim 1 wherein said analyzer further includes a base disposed between said chamber and said evaluation unit, said chamber capable of being assembled to said base.

5. The automatic analyzer of claim 4 wherein said chamber is removable from said base.

6. The automatic analyzer of claim 1 wherein said chamber is disposed in a unit that includes two risers that provide inlet openings for said chamber.

7. The analyzer of claim 6 wherein said risers extend parallel to said chamber before turning toward and intersecting said chamber.

8. The automatic analyzer of claim 6 wherein said unit has a plane bottom which engages with said base and thereupon forms connections to said outlet opening and said risers.

9. The automatic analyzer of claim 8 wherein said connections are provided with exchangeable sealing means.

10. The automatic analyzer of claim 3 further including an additional outlet opening that intersects said bore and extends transversally therefrom.

11. The automatic analyzer of claim 1 further including a fluid sensor between said chamber and said evaluation unit for detecting the flow of passing liquid.

12. The automatic analyzer of claim 2 wherein said chamber is made of a transparent material.

* * * * *

UNITED STATES PATENT AND TRADEMARK OFFICE
CERTIFICATE OF CORRECTION

PATENT NO. : 6,548,022 B1
DATED : April 15, 2003
INVENTOR(S) : Urs Kenel et al.

It is certified that error appears in the above-identified patent and that said Letters Patent is hereby corrected as shown below:

<u>Column 4,</u>
Lines 35-41, please delete claim 3 and replace it with -- 3. The automatic analyzer of claim 1, wherein said chamber has walls that taper to form a bore and then abruptly transition to form said outlet opening, said bore having a larger cross-section than that of said outlet opening and said trap being formed by the substantially abrupt transition between said bore and said outlet opening. --.

Signed and Sealed this

Twentieth Day of September, 2005

JON W. DUDAS
*Director of the United States Patent and Trademark Office*